United States Patent
DeLuca et al.

(10) Patent No.: US 6,939,868 B2
(45) Date of Patent: Sep. 6, 2005

(54) USE OF 2α-METHLY-19-NOR-20(S)-1α,25-DIHYDROXYVITAMIN $D_3$ TO INCREASE BONE STRENGTH

(75) Inventors: Hector F. DeLuca, Deerfield, WI (US); Connie M. Smith, Blue Mounds, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 38 days.

(21) Appl. No.: 10/673,618

(22) Filed: Sep. 29, 2003

(65) Prior Publication Data

US 2004/0072804 A1 Apr. 15, 2004

Related U.S. Application Data

(62) Division of application No. 10/045,941, filed on Oct. 19, 2001, now abandoned, which is a division of application No. 09/616,778, filed on Jul. 14, 2000, now Pat. No. 6,306,844, which is a division of application No. 09/135,463, filed on Aug. 17, 1998, now Pat. No. 6,127,559, which is a division of application No. 08/819,694, filed on Mar. 17, 1997, now Pat. No. 5,945,410.

(51) Int. Cl.[7] ............................................. A61K 31/59
(52) U.S. Cl. ...................................................... 514/167
(58) Field of Search .......................................... 514/167

(56) References Cited

U.S. PATENT DOCUMENTS

| | | | |
|---|---|---|---|
| 4,666,634 A | 5/1987 | Miyamoto et al. | 260/397 |
| 5,086,191 A | 2/1992 | DeLuca et al. | 552/653 |
| 5,237,110 A | 8/1993 | DeLuca et al. | 568/665 |
| 5,246,925 A | 9/1993 | DeLuca et al. | 514/167 |
| 5,536,713 A | 7/1996 | Deluca et al. | 514/167 |
| 5,587,497 A | 12/1996 | DeLuca et al. | 552/653 |
| 5,945,410 A | 8/1999 | DeLuca et al. | 514/167 |

FOREIGN PATENT DOCUMENTS

| | | |
|---|---|---|
| EP | 0184206 | 12/1985 |
| EP | 0078704 | 4/1987 |
| EP | 0387077 | 9/1990 |
| EP | 0480572 | 4/1992 |
| EP | 0474517 | 11/1992 |
| EP | 0516410 | 12/1992 |
| WO | WO90/09991 | 9/1990 |
| WO | WO96/01811 | 1/1996 |

OTHER PUBLICATIONS

Posner et al, "2–Fluoroalkyl A–Ring Analogs of 1,25–Dihydroxyvitamin $D_3$–Stereocontrolled Total Synthesis via Intramolecular and Intermolecular Diels–Alder Cycloadditions. Preliminary Biological Testing", *Journal of Organic Chemisty*, 60, pp. 4617–4628, 1995.

(Continued)

*Primary Examiner*—San-Ming Hui
(74) *Attorney, Agent, or Firm*—Andrus, Sceales, Starke & Sawall, LLP

(57) ABSTRACT

This invention provides pharmaceutical uses for 2α-methyl-19-nor-20(S)-1α,25-dihydroxyvitamin $D_3$. This compound is characterized by high bone calcium mobilization activity demonstrating preferential activity on bone. This results in a novel therapeutic agent for the treatment of diseases where bone formation is desired, particularly osteoporosis. This compound also exhibits pronounced activity in arresting the proliferation of undifferentiated cells and inducing their differentiation to the monocyte thus evidencing use as an anti-cancer agent and for the treatment of skin diseases such as psoriasis. This compound also increases both breaking strength and crushing strength of bones evidencing use in conjunction with bone replacement surgery such as hip and knee replacements.

5 Claims, 3 Drawing Sheets

OTHER PUBLICATIONS

Slatopolsky et al, "A New Analog of Calcitriol, 19–Nor–1, 25–$(OH)_2$ $D_2$ Suppresses Parathyroid Hormone Secretion in Uremic Rats in the Absence of Hypercalcemia", *American Journal of Kidney Disorders*, 26(5), 832–60, 1995.

Posner et al, "Stereocontrolled Synthesis of a Trihydroxylated A Ring as an Immediate Precursor to $I\alpha$, $2\alpha,25$–Trihydroxyvitamin $D^3$", *Journal of Organic Chemistry*, 56, pp. 4339–4341, Apr. 15, 1995.

Chemical Abstracts, "Chemistry of Synthetic High Polymers", vol. 110, No. 10, Abstract 110: 82505v, Mar. 6, 1989.

Okano et al, "Regulatory Activities of $2\beta$–(3–Hydroxypropoxy)–$1\alpha,25$–Dihydroxyvitamin $D_3$. A Novel Synthetic Vitamin $D_3$ Derivative on Calcium Metabolism", *Biochemical and Biophysical Research Communications*, vol. 163, No. 3, pp. 1444–1449, Sep. 29, 1989.

Bouillon et al, "Biological Activity of Dihydroxylated 19–Nor–(Pre)Vitimin $D_3$", *Bioactivity of 19–Nor–Pre D*, vol. 8, No. 8, pp. 1009–1015, 1993.

Sarandeses et al, "Synthesis of $1\alpha,25$–Dihydroxy–19–Nor–previtamin $D_3$", *tetrahedron Letters*, pp. 5445–5448, Apr. 1992.

Perlman et al, "$1\alpha,25$–Dihydroxy–19–Nor–Vitamin $D_3$. A Novel Vitamin D–Related Compound with Potential Therapeutic Activity", *Tetrahedron Letters*, vol. 31, No. 13, pp. 1823–1824, Feb. 1990.

Baggiolini et al, "Stereochemical Total Synthesis of $1\alpha,25$–Dihydroxycholecalciferol and $1\beta,25$–Dihydroxyerocalciferol", *Journal of Organic Chemistry*, 51, pp. 3098–3108, 1986.

Kiegiel et al, "Chemical Conversion of Vitamin $D_3$ to its 1,25–Dihydroxy Metabolite", *Tetrahedron Letters*, vol. 31, No. 43, pp. 6057–60660, 1991.

Peacock, Journal of Bone and Mineral Research, 1991, vol. 6, Supplement 2, pp. S77–S84.

Hoiseth et al, Acta Radiologica, 1990, vol. 31, No. 6, pp. 626–627.

Merck Manual, 16th Ed., 1992, p. 1357.

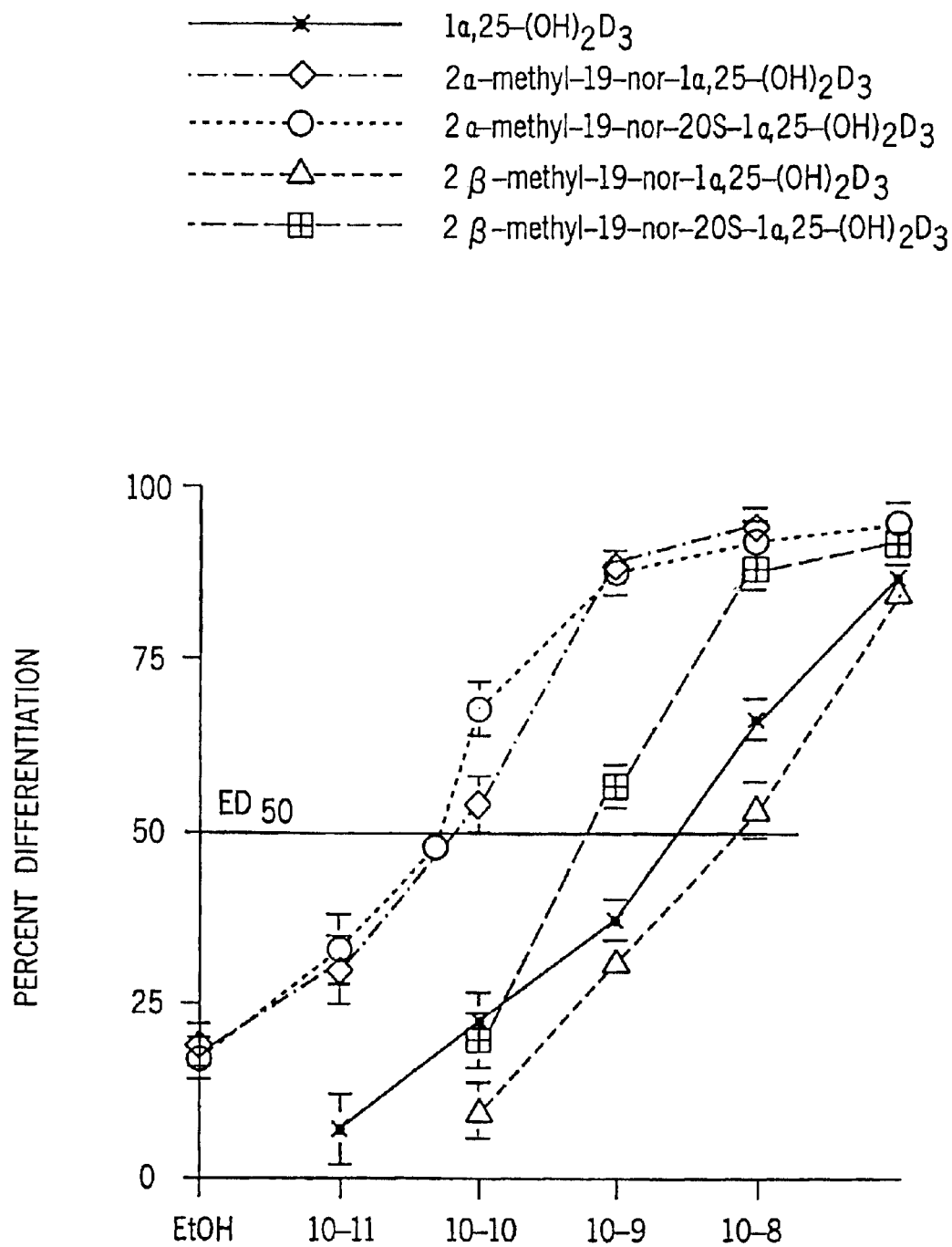
FIG. 3    MOLAR CONCENTRATION

USE OF 2α-METHLY-19-NOR-20(S)-1α,25-DIHYDROXYVITAMIN D₃ TO INCREASE BONE STRENGTH

This is the divisional of Ser. No. 10/045,941, filed Oct. 19, 2001 now abandoned, which is a divisional of Ser. No. 09/616,778, filed Jul. 14, 2000 now U.S. Pat. No. 6,306,844, which is a continuation-in-part of Ser. No. 09/135,463, filed Aug. 17, 1998 now U.S. Pat. No. 6,127,559, which is a continuation-in-part of Ser. No. 08/819,694, filed Mar. 17, 1997 now U.S. Pat. No. 5,945,410.

BACKGROUND OF THE INVENTION

This invention relates to vitamin D compounds, and more particularly to pharmaceutical uses for 2α-methyl-19-nor-20(S)-1α,25-dihydroxyvitamin $D_3$.

The natural hormone, 1α,25-dihydroxyvitamin $D_3$ and its analog in ergocalciferol series, i.e. 1α,25-dihydroxyvitamin $D_2$ are known to be highly potent regulators of calcium homeostasis in animals and humans, and more recently their activity in cellular differentiation has been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

Recently, a new class of vitamin D analogs has been discovered, i.e. the so called 19-nor-vitamin D compounds, which are characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Left. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

Recently, 2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, an analog which is characterized by the presence of a methyl substituent at the carbon 2 (C-2) has been synthesized and tested. Of particular interest is the analog which is characterized by the unnatural configuration of the methyl group at carbon 20 (C-20), i.e. 2α-methyl-19-nor-20(S)-1α,25-dihydroxyvitamin $D_3$. This vitamin D analog seemed an interesting target because the relatively small methyl group at C-2 should not interfere with the vitamin D receptor. Moreover, molecular mechanics studies performed on the model 1α-hydroxy-2-methyl-19-nor-vitamins indicate that such molecular modification does not change substantially the conformation of the cyclohexanediol ring A. However, introduction of the 2-methyl group into 19-nor-vitamin D carbon skeleton changes the character of its 1α- and 3β-A-ring hydroxyls. Both hydroxyls are allylic to the exocyclic methylene group similar to the 1α-hydroxyl group (crucial for biological activity) in the molecule of the natural hormone, 1α,25-$(OH)_2D_3$.

SUMMARY OF THE INVENTION

The present invention is directed toward 2α-methyl-19-nor-20(S)-1α,25-dihydroxyvitamin $D_3$, its biological activity, and various pharmaceutical uses for this compound.

Structurally this 19-nor analog is characterized by the general formula I shown below:

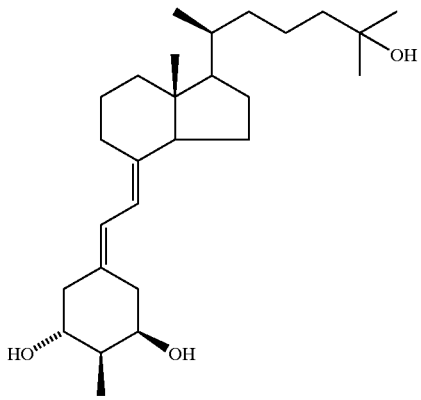

The solid wedge-shaped line to the methyl substituent at C-20 indicates that carbon 20 has the S configuration.

The above compound exhibits a desired, and highly advantageous, pattern of biological activity. This compound is characterized by intestinal calcium transport activity equal to that of 1α,25-dihydroxyvitamin $D_3$, but exhibiting relatively high activity, as compared to 1α,25-dihydroxyvitamin $D_3$, in its ability to mobilize calcium from bone. Hence, this compound is highly specific in its calcemic activity. Its preferential activity on mobilizing calcium from bone allows the in vivo administration of this compound for the treatment of metabolic bone diseases where bone loss is a major concern. Because of its preferential activity on bone, this compound would be a preferred therapeutic agent for the treatment of diseases where bone formation is desired, such as osteoporosis, especially low bone turnover osteoporosis, steroid induced osteoporosis, senile osteoporosis or postmenopausal osteoporosis, as well as osteomalacia and renal osteodystrophy. The treatment may be transdermal, oral or parenteral. The compound may be present in a composition in an amount from about 0.1 μg/gm to about 50 μg/gm of the composition, and may be administered in dosages of from about 0.1 μg/day to about 10 μg/day.

The compound of the invention is also especially suited for treatment and prophylaxis of human disorders which are characterized by an imbalance in the immune system, e.g. in autoimmune diseases, including multiple sclerosis, diabetes mellitus, host versus graft reaction, and rejection of transplants; and additionally for the treatment of inflammatory diseases, such as rheumatoid arthritis and asthma, as well as the improvement of bone fracture healing and improved bone grafts. Acne, alopecia, skin conditions such as dry skin (lack of dermal hydration), undue skin slackness (insufficient skin firmness), insufficient sebum secretion and wrinkles, and hypertension are other conditions which may be treated with the compound of the invention.

The above compound is also characterized by high cell differentiation activity. Thus, this compound also provides a therapeutic agent for the treatment of psoriasis, or as an anti-cancer agent, especially against leukemia, colon cancer, breast cancer and prostate cancer. The compound may be present in a composition to treat psoriasis in an amount from about 0.01 μg/gm to about 50 μg/gm of the composition, and may be administered topically, transdermally, orally or parenterally in dosages of from about 0.01 μg/day to about 10 μg/day.

It has also been discovered that this compound increases breaking strength (cortical strength) as well as crushing strength (trabecular strength) of bones. Thus, this compound could also be used in conjunction with bone replacement procedures such as hip replacements, knee replacements, and the like.

BRIEF DESCRIPTION OF THE DRAWINGS

FIG. 3 is a graph illustrating the percent HL-60 cell differentiation as a function of the concentration of 2α-methyl-19-nor-20(S)-1α,25-dihydroxyvitamin $D_3$, 2α-methyl-19-nor-1α,25-dihydroxyvitamin $D_3$ and 1α,25-dihydroxyvitamin $D_3$.

DETAILED DESCRIPTION OF THE INVENTION

2α-methyl-19-nor-20(S)-1α,25-dihydroxyvitamin $D_3$(referred to herein as 2AMD) was synthesized and tested. Structurally, this 19-nor analog is characterized by the general formula I previously illustrated herein.

The preparation of 2α-methyl-19-nor-20(S)-1α,25-dihydroxyvitamin $D_3$ having the basic structure I can be accomplished by a common general method, i.e. the condensation of a bicyclic Windaus-Grundmann type ketone II with the allylic phosphine oxide III to the corresponding 2-methylene-19-nor-vitamin D analog IV followed by selective reduction of the exomethylene group at C-2 and deprotection at C-1 and C-3 in the latter compound:

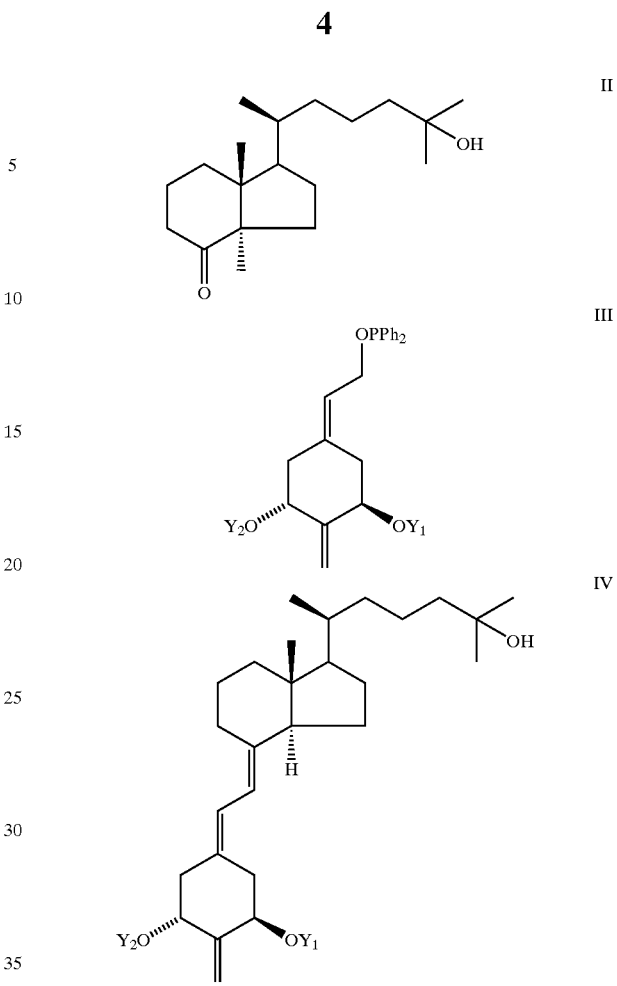

In the structures II, III, and IV groups $Y_1$ and $Y_2$ are hydroxy-protecting groups, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

Hydrindanones of the general structure II are known, or can be prepared by known methods.

For the preparation of the required phosphine oxides of general structure III, a new synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compound I is illustrated and described more completely in U.S. Pat. No. 5,945,410 issued Aug. 31, 1999 and entitled "2-Alkyl-19-Nor-Vitamin D Compounds" the specification of which is specifically incorporated herein by reference.

Biological Activity of 2α-methyl-20(S)-19-nor-1,25-(OH)$_2$D$_3$

Figure 1:
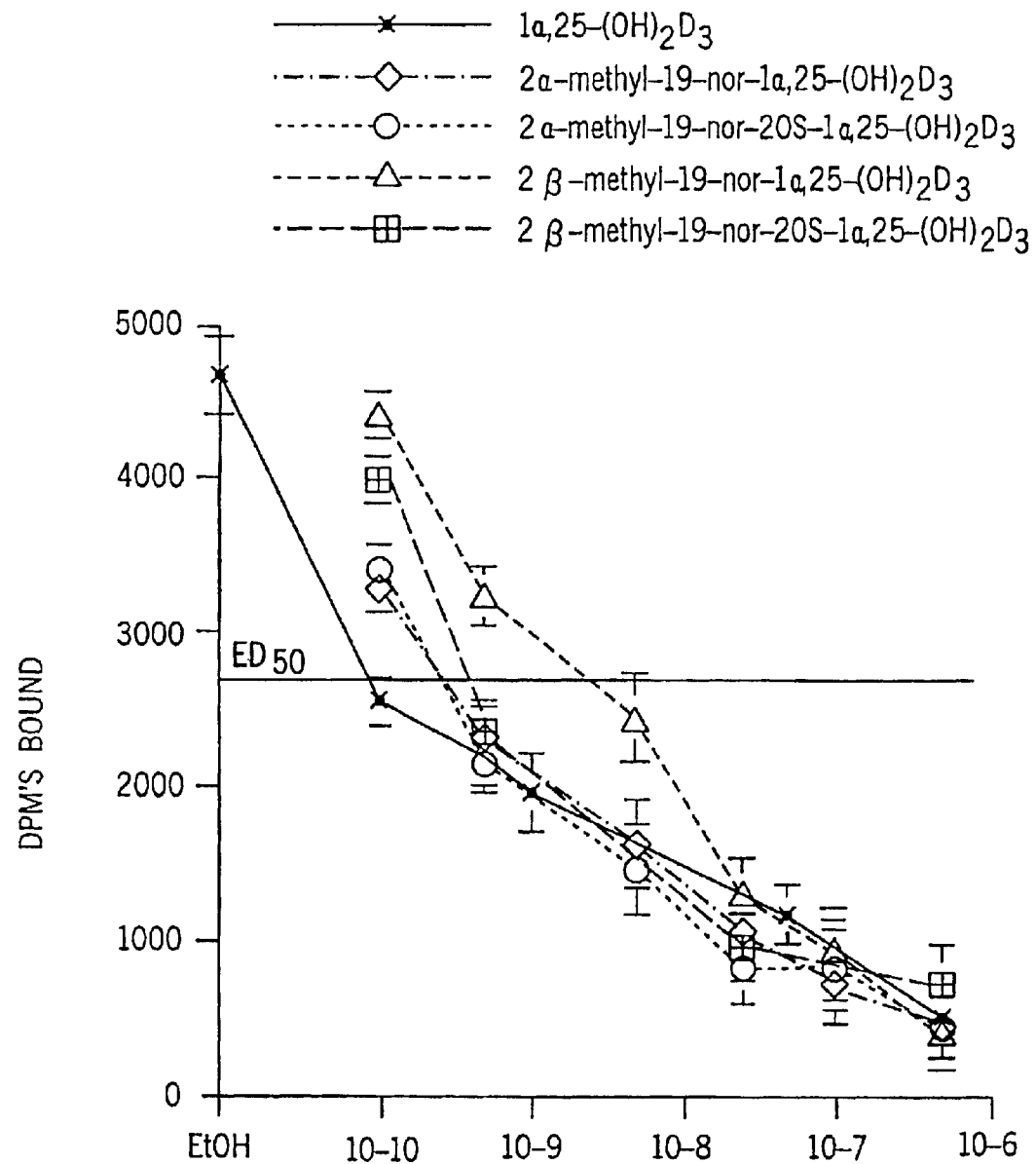
FIG. 1 is a graph illustrating the relative activity of 2α-methyl-19-nor-20(S)-1α,25-dihydroxyvitamin $D_3$, 2α-methyl-19-nor-1α,25-dihydroxyvitamin $D_3$ and 1α,25-dihydroxyvitamin $D_3$ to compete for binding of [$^3$H]-1,25-(OH)$_2$-$D_3$ to the vitamin D pig intestinal nuclear receptor.

The introduction of a methyl group in the 2α-position of the 20(S) isomer of 19-nor-1,25-(OH)$_2$D$_3$ had little or no effect on binding to the porcine intestinal vitamin D receptor. This compound bound equally well to the porcine receptor as compared to the standard 1,25-(OH)$_2$D$_3$ (FIG. 1). It might be expected from these results that this compound would have equivalent biological activity. Surprisingly, however, the 2α-methyl and 20(S) substitutions produced a highly selective analog with its primary action on bone.

Figure 2:
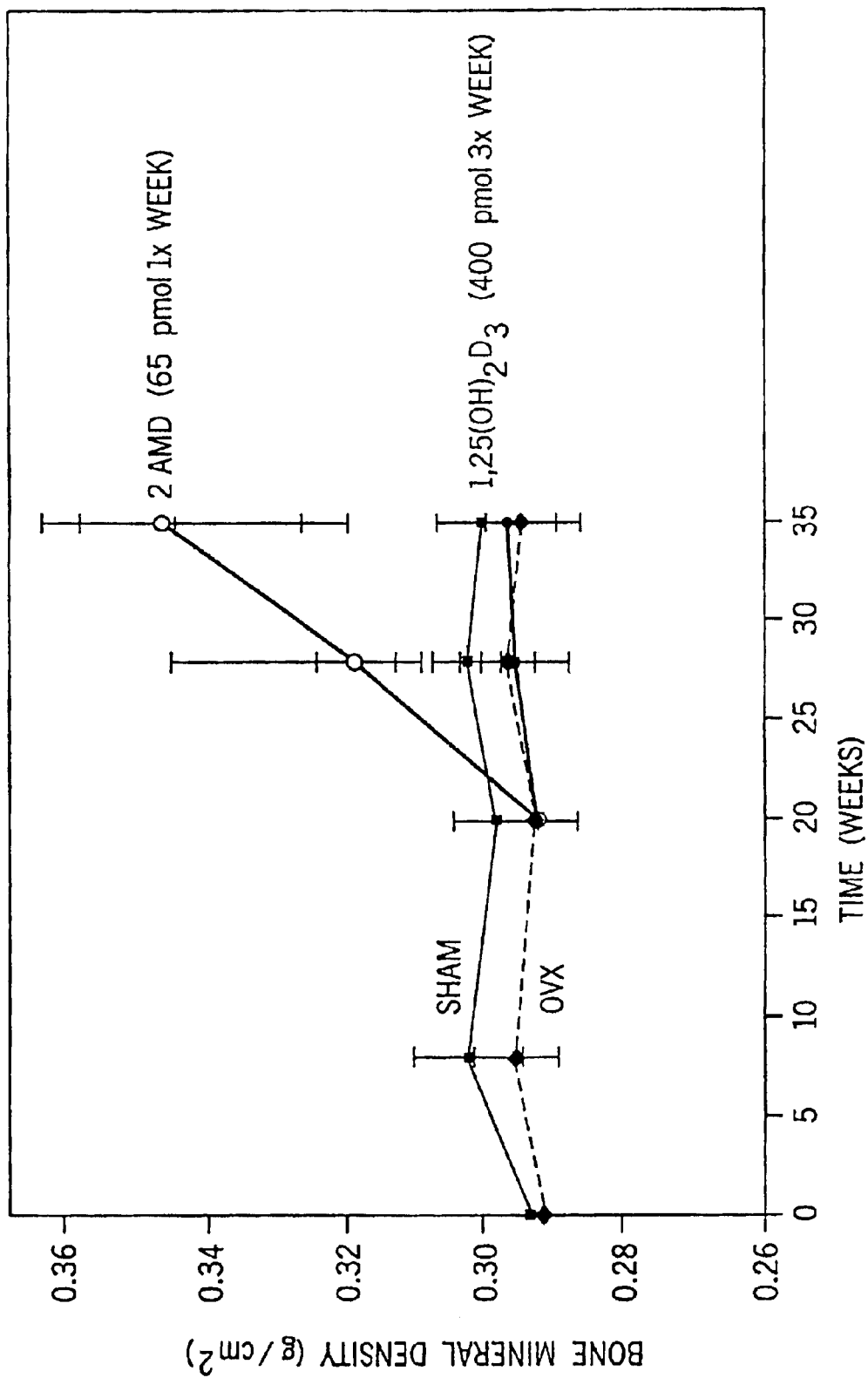
FIG. 2 is a graph illustrating the bone mineral density in ovariectomized old female rats as a result of treatment with 2α-methyl-19-nor-20(S)-1α,25-dihydroxyvitamin $D_3$ as compared to 1α,25-dihydroxyvitamin $D_3$.

FIG. 2 shows that 2AMD is extraordinarily effective in building bone mass in ovariectomized rats as compared to the native hormone without increasing serum calcium concentration. This is as yet an unprecedented new finding for a vitamin D compound.

FIG. 3 illustrates that 2AMD is 50–100 times more potent than 1,25(OH)$_2$D$_3$ on HL-60 differentiation, making it an excellent candidate for the treatment of psoriasis and cancer, especially against leukemia, colon cancer, breast cancer and prostate cancer.

Table 1 illustrates that 2AMD is very effective in restoring bone of ovariectomized, old female rats at 32 pmol given 2 times per week as compared to 1,25(OH)$_2$D$_3$ given at high doses 3 times per week. Note: 2AMD also increases % ash in the femur.

Table 2 shows that 2AMD increases breaking strength in the femurs (cortical strength) and crushing strength in the vertebra (trabecular strength) of animals shown in Table 1.

Table 3 shows that 2AMD has selective activity on bone.

Competitive binding of the analogs to the porcine intestinal receptor was carried out by the method described by Dame et al (Biochemistry 25, 4523–4534, 1986).

The differentiation of HL-60 promyelocytic into monocytes was determined as described by Ostrem et al (J. Biol. Chem. 262, 14164–14171, 1987).

Interpretation of Data

2AMD is about as active as 1,25(OH)$_2$D$_3$ in binding to the vitamin D receptor (FIG. 1). However, it is between 10–100 times more active than 1,25-(OH)$_2$D$_3$ in causing differentiation of the promyelocyte, HL-60, into the monocyte (FIG. 3). This result suggests that 2AMD will be very effective in psoriasis because it has direct cellular activity in causing differentiation and in suppressing growth. It also indicates that it will have significant activity as an anti-cancer agent, especially against leukemia, colon cancer, breast cancer and prostate cancer, or as an agent in the treatment of psoriasis.

The most important result, however, is that 2AMD is extremely effective not only in restoring bone mass of ovariectomized, old female breeder rats as shown in FIG. 2 and Tables 1 and 2, but it causes an increase in bone mass above that of sham-operated controls. This illustrates that 2AMD is very likely having an anabolic effect on bone or increasing bone formation. Importantly, the increased bone mass provided by 2AMD translates into marked increases in bone strength. This increased strength to fracture in femur shows cortical strength while increased strength to crush fractures of vertebra illustrates trabecular bone strength (Table 2). Interestingly, even the percent ash is unexpectedly increased further by 2AMD. Of great importance is that at the dosage levels used in this study, there was no change in serum calcium of animals that showed the marked elevation of bone mass. This argues that a window of safety exists between the use of 2AMD to increase bone mineral content and the action of 2AMD in elevating serum calcium.

When given for 7 days in a chronic mode, the most potent individual compound tested was 2α-methyl 19-nor-20S-1,25-(OH)$_2$D$_3$ (Table 3). When given at 130 pmol/day, the activity of this compound on bone calcium mobilization (serum calcium) was much higher than that of the native hormone, possible as high as 10 or 100 times higher. Under identical conditions, twice the dose of 1,25-(OH)$_2$D$_3$ gave a serum calcium value of 6.6±0.4 mg/100 ml, while 2α-methyl-19-nor-20S-1,25-(OH)$_2$D$_3$ gave a value of 8.3±0.7 mg/100 ml of serum calcium at the 130 pmol dose. When given at 260 pmol/day, 2α-methyl-19-nor-20S-1,25-(OH)$_2$D$_3$ produced the astounding value of 10.3±0.11 mg/100 ml of serum calcium at the expense of bone. To show its selectivity, this compound also produced a significant change in intestinal calcium transport at both the 260 pmol and the 130 pmol dose levels while having a strong bone calcium mobilizing activity. At the higher dose, the 2α-methyl-20(S) compound did produce a significant intestinal transport response but also gave an enormous bone mobilization response. With respect to the 2β-methyl-19-nor-20(S) compound, the data in Table 3 show it has little, if any, intestinal calcium transport activity, and little, if any, bone mobilization activity. Thus, the 2α-methyl-19-nor-20(S)-derivative showed strong preferential bone calcium mobilizing activity. These results illustrate that the 20(S)-2α-methyl derivative of 19-nor-1,25-(OH)$_2$D$_3$ is selective for mobilization of calcium from bone.

These results illustrate that 2AMD is an excellent candidate for an anti-osteoporosis therapy and that it may be useful in a number of other circumstances such as autoimmune diseases, cancer, and psoriasis.

TABLE 1

Treatment of Ovariectomized Rats with 1,25-(OH)$_2$D$_3$ and 2AMD

| Group | Treatment | Treatment Time (Weeks) | BMD (g/cm$^2$) | BMC (g) | Body Wt. (g) | BMC/Body Wt. (mg/g) | Serum CA (mg/dl) | Femur Ash (%) | Femur Ash (mg) |
|---|---|---|---|---|---|---|---|---|---|
| OVX Control | Oil Vehicle/5x/Week | 8 | 0.294 ± 0.004 | 8.64 ± 3.30 | 414 ± 15 | 21.4 ± 1.20 | — | — | — |
| | | 17 | 0.296 ± 0.003 | 9.34 ± 0.50 | 422 ± 19 | 22.3 ± 1.69 | — | — | — |
| | | 30 | 0.296 ± 0.003 | 9.41 ± 0.45 | 404 ± 24 | 23.4 ± 1.60 | 11.1 ± 0.17 | 59.2 ± 0.82 | 386 ± 21.6 |
| Sham Operated | Oil Vehicle/5x/Week | 8 | 0.302 ± 0.003 | 9.34 ± 0.38 | 356 ± 14 | 26.3 ± 0.76 | | | |
| | | 17 | 0.300 ± 0.002 | 9.14 ± 0.54 | 351 ± 15 | 26.4 ± 0.82 | | | |
| | | 30 | 0.297 ± 0.004 | 9.20 ± 0.53 | 340 ± 13 | 26.7 ± 1.20 | 11.8 ± 0.20 | 81.5 ± 1.20 | 400 ± 18.0 |

TABLE 1-continued

Treatment of Ovariectomized Rats with 1,25-(OH)$_2$D$_3$ and 2AMD

| Group | Treatment | Treatment Time (Weeks) | BMD (g/cm$^2$) | BMC (g) | Body Wt. (g) | BMC/Body Wt. (mg/g) | Serum CA (mg/dl) | Femur Ash (%) | Femur Ash (mg) |
|---|---|---|---|---|---|---|---|---|---|
| 1,25(OH)$_2$D$_3$ | 250 pmol/d/5x/Week | 8 | 0.297 ± 0.001 | 8.90 ± 0.40 | 399 ± 9.3 | 22.4 ± 0.48 | | | |
| | | 17 | 0.308 ± 0.008 | 9.6 ± 0.39 | 394 ± 11 | 24.5 ± 0.87 | | | |
| | | 30 | 0.310 ± 0.007 | 10.1 ± 0.30 | 392 ± 16 | 26.1 ± 0.97 | 11.4 ± 0.21 | 60.8 ± 1.1 | 417 ± 23 |
| 1,25(OH)$_2$D$_3$ | 500 pmol/d/5x/Week | 8 | 0.312 ± 0.005 | 10.2 ± 0.40 | 397 ± 14.2 | 26.3 ± 0.57 | | | |
| | 3x/Week | 17 | 0.331 ± 0.008 | 11.5 ± 0.25 | 421 ± 12.8 | 27.6 ± 0.68 | | | |
| | 3x/Week | 30 | 0.328 ± 0.003 | 11.8 ± 0.23 | 432 ± 23.0 | 28.0 ± 0.69 | 11.9 ± 0.20 | 61.4 ± 1.3 | 478 ± 7.5 |
| 2AMD | 32 pmol/d/2x/Week | 8 | 0.297 ± 0.002 | 11.2 ± 0.55 | 371 ± 13.5 | 31.0 ± 2.50 | | | |
| | | 17 | 0.308 ± 0.001 | 9.7 ± 0.24 | 401 ± 9.6 | 24.2 ± 1.04 | | | |
| | | 30 | 0.320 ± 0.003 | 11.2 ± 0.55 | 371 ± 13.5 | 31.0 ± 2.50 | 10.4 ± 0.53 | 61.7 ± 1.2 | 447 ± 23.3 |
| 2AMD | 65 pmol/d/1x/Week | 8 | 0.298 ± 0.002 | 9.1 ± 0.31 | 384 ± 9.7 | 23.9 ± 0.37 | | | |
| | | 17 | 0.308 ± 0.004 | 9.5 ± 0.57 | 396 ± 12.8 | 24.3 ± 0.53 | | | |
| | | 30 | 0.308 ± 0.003 | 9.7 ± 0.28 | 387 ± 13.7 | 25.1 ± 1.00 | 10.8 ± 0.22 | 60.0 ± 1.4 | 403 ± 12. |

All animals were ovariectomized except the sham-operated controls. Values are expressed as mean ± SEM.

TABLE 2

Strength of Femurs and Vertebrae to Mechanical Stress

| Group | Treatment | Stress Value Femur | Stress Value Vertebra |
|---|---|---|---|
| OVX Control | Oil Vehicle/5x/Week | 109.31 ± 19.60 | 14.26 ± 3.58 |
| Sham-Operated | Oil Vehicle/5x/Week | 121.36 ± 12.5 | 13.67 ± 1.79 |
| 1,25(OH)$_2$D$_3$ | 250 pmol/day/5x/Week | 118.21 ± 19.85 | 19.24 ± 5.66 |
| 1,25(OH)$_2$D$_3$ | 500 pmol/d/3–5x/Week | 116.47 ± 16.20 | 17.14 ± 0.52 |
| 2AMD | 32 pmol/d/2x/Week | 132.19 ± 19.69 | 20.22 ± 8.53 |
| 2AMD | 65 pmol/d/1x/Week | 114.08 ± 21.71 | 17.13 ± 4.67 |

TABLE 3

Response of Intestinal Calcium Transport and Serum Calcium (Bone Calcium Mobilization) Activity to Chronic Doses of the 20(S) Isomers of 2-Methyl Derivatives of 19-Nor-1,25-(OH)$_2$D$_3$

| Group | Dose (pmol/day/7 days) | Intestinal Calcium Transport (S/M) | Serum Calcium (mg/100 ml) |
|---|---|---|---|
| Vitamin D Deficient | Vehicle | 2.9 ± 0.2 | 4.2 ± 0.1 |
| 1,25-(OH)$_2$D$_3$ Treated | 260 | 4.6 ± 0.2 | 6.6 ± 0.4 |
| 2α-Methyl-19-Nor-20(S)-1,25-(OH)$_2$D$_3$ | 130 | 12.9 ± 1.9 | 8.3 ± 0.7 |
| | 260 | 8.4 ± 1.1 | 10.3 ± 0.11 |
| 2β-Methyl-19-nor-20(S)-1,25-(OH)$_2$D$_3$ | 130 | 2.9 ± 0.3 | 4.4 ± 0.1 |
| | 260 | 3.8 ± 0.1 | 4.4 ± 0.1 |

With respect to the data in Table 3, male weanling rats were obtained from Sprague Dawley Co. (Indianapolis, Ind.) and fed a 0.47% calcium, 0.3% phosphorus vitamin D-deficient diet for 1 week and then given the same diet containing 0.02% calcium, 0.3% phosphorus for 2 weeks. During the last week they were given the indicated dose of compound by intraperitoneal injection in 0.1 ml 95% propylene glycol and 56/o ethanol each day for 7 days. The control animals received only the 0.1 ml of 95% propylene glycol, 5% ethanol. Twenty-four hours after the last dose, the rats were sacrificed and intestinal calcium transport was determined everted sac technique as previously described and serum calcium determined by atomic absorption spectrometry on a model 3110 Perkin Elmer instrument (Norwalk, Conn.). There were 5 rats per group and the values represent mean±SEM.

For treatment purposes, the compound of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compound may be administered orally, topically, parenterally or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.1 μg to 10 μg per day of the compounds are appropriate for treatment purposes, such doses being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin D$_2$ or D$_3$, or 1α,25-dihydroxyvitamin D$_3$—in situations where different degrees of bone mineral mobilization and calcium transport stimulation is found to be advantageous.

Compositions for use in the above-mentioned treatment of psoriasis and other malignancies comprise an effective amount of the 2α-methyl-20(S)-19-nor-vitamin D compound as defined by the above formula I as the active ingredient, and a suitable carrier. An effective amount of such compound for use in accordance with this invention is from about 0.01 μg to about 50 μg per gm of composition, and may be administered topically, transdermally, orally or parenterally in dosages of from about 0.1 μg/day to about 10 μg/day.

The compound may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compound is advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A method of treating leukemia, colon cancer, breast cancer or prostate cancer comprising administering to a patient with said disease an effective amount of 2α-methyl-19-nor-20(S)-1α,25-dihydroxyvitamin $D_3$ having the formula:

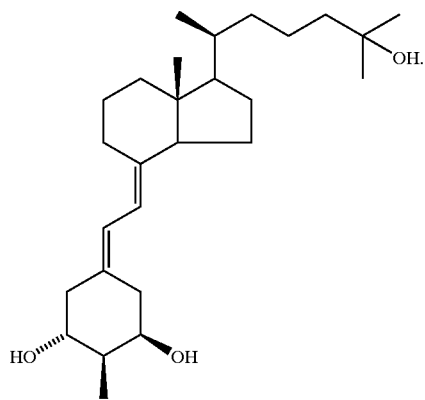

2. The method of claim 1 wherein 2α-methyl-19-nor-20 (S)-1α,25-dihydroxyvitamin $D_3$ is administered orally.

3. The method of claim 1 wherein 2α-methyl-19-nor-20 (S)-1α,25-dihydroxyvitamin $D_3$ is administered parenterally.

4. The method of claim 1 wherein 2α-methyl-19-nor-20 (S)-1α,25-dihydroxyvitamin $D_3$ is administered transdermally.

5. The method of claim 1 wherein 2α-methyl-19-nor-20 (S)-1α,25-dihydroxyvitamin $D_3$ is administered in a dosage of from about 0.01 μg/day to about 10 μg/day.

* * * * *

UNITED STATES PATENT AND TRADEMARK OFFICE
CERTIFICATE OF CORRECTION

PATENT NO. : 6,939,868 B2
DATED : September 9, 2005
INVENTOR(S) : Hector F. DeLuca et al.

It is certified that error appears in the above-identified patent and that said Letters Patent is hereby corrected as shown below:

Title page,
Item [54], Title, delete the word "METHLY" and substitute therefor -- METHYL --.
Item [62], Related U.S. Application Data, delete the phrase "division of application No. 09/135,463" and substitute therefor -- continuation-in-part of application No. 09/135,463 --; and delete the phrase "division of application No. 08/819,694" and substitute therefor -- continuation-in-part of application No. 08/819,694 --.

Signed and Sealed this

Twenty-fifth Day of October, 2005

JON W. DUDAS
*Director of the United States Patent and Trademark Office*